United States Patent [19]
Wilk et al.

[11] Patent Number: 5,236,437
[45] Date of Patent: Aug. 17, 1993

[54] SURGICAL INSTRUMENT ASSEMBLY AND ASSOCIATED TECHNIQUE

[76] Inventors: Peter J. Wilk, 185 West End Ave., New York, N.Y. 10023; Jonathan Tiefenbrun, 62 Country Rd., Mamaroneck, N.Y. 10543

[21] Appl. No.: 914,161

[22] Filed: Jul. 14, 1992

[51] Int. Cl.[5] .............................................. A61B 17/28
[52] U.S. Cl. ..................................... 606/207; 606/158
[58] Field of Search ............... 606/119, 120, 121, 122, 606/124, 127, 128, 191, 192, 198, 201-203, 205-211; 81/83, 483; 294/99.2

[56] References Cited

U.S. PATENT DOCUMENTS

| | | | |
|---|---|---|---|
| 2,549,731 | 4/1951 | Wattley | 606/206 |
| 2,637,320 | 5/1953 | Greenberg | 606/127 |
| 3,503,397 | 3/1970 | Fogarty et al. | 606/207 |
| 3,675,656 | 7/1972 | Hakim | 606/202 |
| 4,586,501 | 5/1986 | Claracq | 606/158 |
| 4,708,140 | 11/1987 | Baron | 606/201 |

*Primary Examiner*—John D. Yasko
*Assistant Examiner*—William Lewis
*Attorney, Agent, or Firm*—R. Neil Sudol; Henry D. Coleman

[57] ABSTRACT

A surgical instrument assembly comprises an elongate member provided at a distal end with a clamping member having a pair of opposed jaws and at least one balloon element attached to the jaws so as to form a cushion upon inflation of the balloon element. An inflation device is operatively connected to the balloon element for inflating the balloon from a collapsed insertion configuration to an expanded use configuration. A closure device is associated with and at least partially coextensive with the elongate member in a longitudinal direction for closing the clamping member about an object such as a section of colon.

18 Claims, 2 Drawing Sheets

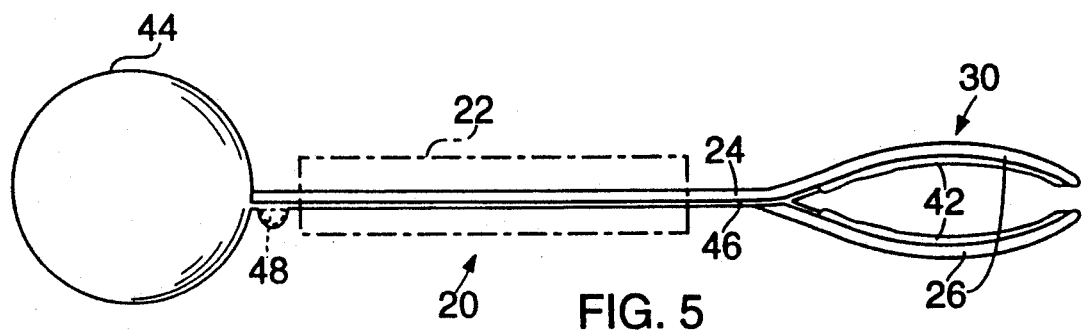
FIG. 5
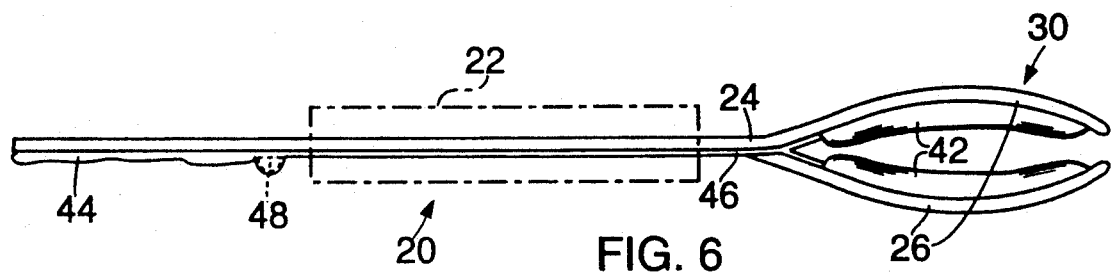
FIG. 6
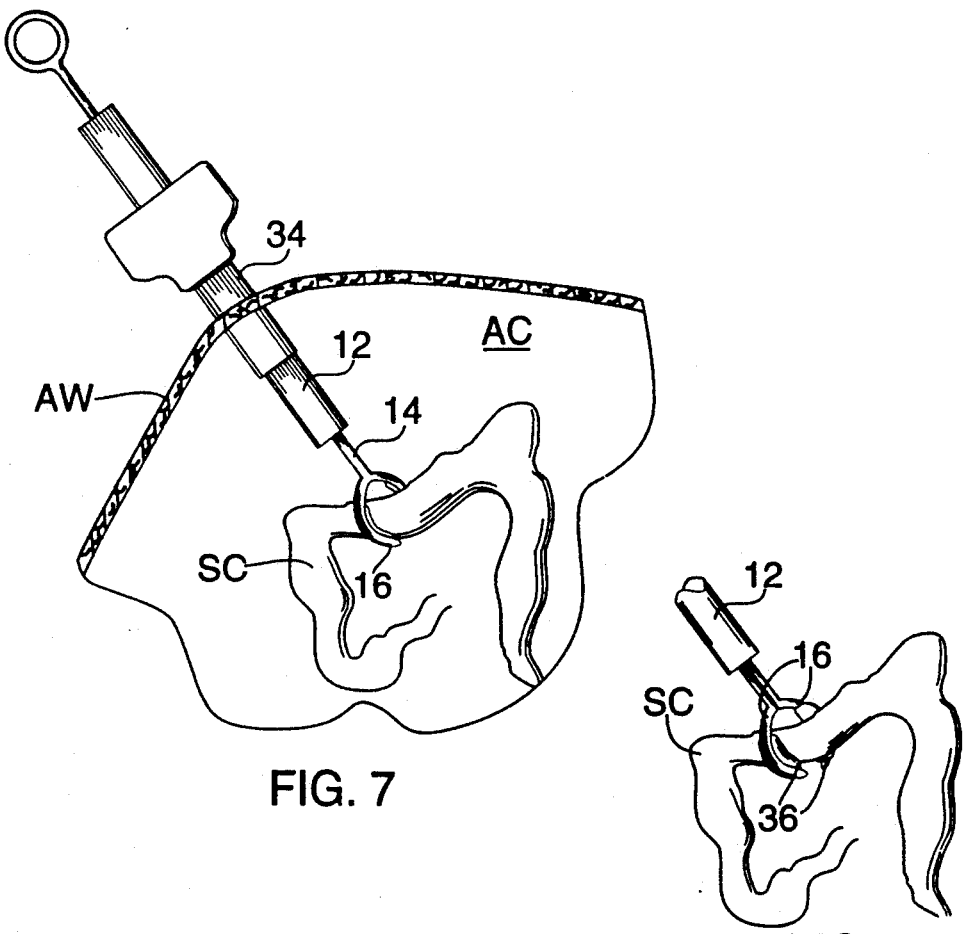
FIG. 7
FIG. 8

SURGICAL INSTRUMENT ASSEMBLY AND ASSOCIATED TECHNIQUE

BACKGROUND OF THE INVENTION

This invention relates to a surgical instrument assembly and an associated surgical technique.

During the performance of laparoscopic operations, it is frequently necessary to move an organ such as an intestine or an artery in order to reach an underlying organ. Such large tubular organs cannot be easily manipulated in laparoscopic surgery. Existing instruments such as grasping forceps have operating tips (e.g., jaws) which are basically too small to grasp a colon or major artery and move the organ without injury thereto.

Existing laparoscopic instruments are also ineffective to clamp large organs such as an intestine or an artery. Such a clamping operation would be helpful in trauma cases, for example, to prevent spillage of fecal matter from a perforated intestine.

OBJECTS OF THE INVENTION

An object of the present invention is to provide a surgical instrument or instrument assembly which may be used to grasp and partially shift larger internal organs of a patient such as the colon or the aorta.

Another, related object of the present invention is to provide such a surgical instrument or instrument assembly which may be used in laparoscopic surgery to grasp and partially shift larger internal organs of a patient such as the colon or the aorta.

An associated object of the present invention is to provide a surgical technique which may be used to grasp and partially shift larger internal organs of a patient such as the colon or the aorta, particularly in laparoscopic surgery but not exclusively limited thereto.

Yet another object of the present invention is to provide a surgical technique and an associated instrument assembly which may be used to clamp larger internal organs of a patient such as the colon or the aorta, particularly in laparoscopic surgery but not exclusively limited thereto.

These and other objects of the present inventions will be apparent from the following descriptions and the drawings.

SUMMARY OF THE INVENTION

A surgical instrument assembly comprises, in accordance with the present invention, an elongate member provided at a distal end with a clamping member having a pair of opposed jaws and at least one balloon element attached to the jaws so as to form a cushion upon inflation of the balloon element. An inflation device is operatively connected to the balloon element for inflating the balloon from a collapsed insertion configuration to an expanded use configuration. A closure device is associated with and at least partially coextensive with the elongate member in a longitudinal direction for closing the clamping member about an object such as a section of colon.

Pursuant to another feature of the present invention, the arms are arcuate and the clamping member is generally C-shaped in an opened configuration. The closure device then operates to press the arms towards one another to partially flatten the arms, thereby closing the clamping member about an object. More specifically, the arms are integral with the elongate member and with one another and are made of a resilient material having a limited degree of flexibility and an internal spring force whereby the arms are maintained in an opened configuration in the absence of a closure force.

According to another feature of the present invention, the closure device includes a tubular member surrounding at least a portion of the elongate member, the tubular member cooperating with the arms in a camming action to press the arms towards one another upon relative motion of the tubular member and the arms towards each other. The elongate member may then take the form of a rod slidably inserted into the tubular member.

Pursuant to yet a further feature of the present invention, the balloon element is one of a pair of balloon elements each attached to a respective one of the jaws.

The inflation device may include an auxiliary balloon attached to the elongate member at a proximal end thereof. Such an inflation device serves to enable control of the degree of inflation of the balloon element or elements.

A surgical instrument assembly comprises, in accordance with the present invention, an elongate tubular member, an elongate rod having at least a portion slidably inserted in the tubular member, and two prongs connected to the rod at a distal end thereof. The prongs each have an arcuate configuration when ejected from a distal end of the tubular member by a distally directed motion of the rod and form a pair of grasping jaws in the ejected configuration. The prongs are flattened out and pressed towards one another upon a shifting of the tubular member over the prongs at a proximal end thereof. At least one balloon element is attached to the prongs so as to form a cushion upon inflation of the balloon element. An inflation device is operatively connected to the balloon element for inflating the balloon from a collapsed insertion configuration to an expanded use configuration.

A surgical method comprises, in accordance with the present invention, the steps of (a) inserting a distal end of an elongate member into a patient's abdomen, (b) upon the step of inserting, opening a pair of opposed arms of a clamping member connected to the elongate member at a distal end thereof, thereby forming a pair of jaws, (c) moving the jaws towards an internal organ of the patient to insert a portion of the organ between the jaws, and (d) inflating a balloon element connected to the jaws, thereby forming a cushion for clamping the organ.

Accordingly, a large internal organ such as a colonic section or a portion of the aorta may be grasped and clamped in a method in accordance with the present invention. In the event of a traumatized or perforated organ such as the colon, the organ may be temporarily clamped on opposite sides of the perforation to prevent the spilling of fecal material into the abdomen, possibly infecting other organs. The perforation may then be repaired or patched.

In an optional step in accordance with the present invention, the organ is displaced relative to other organic tissues of the patient by exerting a force on the tubular member and the jaws. This displacement enables a surgeon to reach underlying tissues which would otherwise be difficult to access.

Preferably, the arms are integral with the elongate member and with one another and are made of a resilient material having a limited degree of flexibility and an internal spring force whereby the arms are maintained in an opened configuration in the absence of a closure force. In that event, the method may further comprise the step of pressing the jaws towards one another to partially flatten the jaws, thereby closing the clamping member about the organ. The step of pressing may include the step of shifting an elongate tubular member towards the jaws to engage the jaws in a camming action and to partially close the jaws in opposition to the internal spring force.

According to another feature of the present invention, the balloon element is one of a pair of balloon elements attached to respective ones of the jaws, the step of inflating comprising the step of inflating the balloon elements simultaneously.

The inflation of the balloon element or elements may be executed prior to or after the positioning of the jaws about an organ to be grasped and moved.

An instrument assembly and surgical method in accordance with the present invention is especially adapted to use in a laparoscopic procedure. In that event, the distal end of the instrument assembly is inserted into the patient's abdomen through a trocar sleeve or laparoscopic cannula which is disposed in and traverses the abdominal wall of the patient.

A surgical instrument or instrument assembly in accordance with the present invention may be used to grasp and partially shift larger internal organs of a patient such as the colon or the aorta. The instrument assembly may also be used as a clamp. For example, where an organ such as the colon is perforated, a pair of instrument assemblies in accordance with the invention may be used to temporarily clamp the colon on opposite sides of the perforation prior to a surgical closure of the perforation.

When a surgical instrument or instrument assembly in accordance with the present invention is used to grasp and partially shift larger internal organs of a patient such as the colon or the aorta, the balloon elements serve to spread the area over which the grasping and clamping forces are exerted, thereby reducing the force at any one location. The balloon elements thereby function to cushion the jaws.

BRIEF DESCRIPTION OF THE DRAWING

FIG. 5 is a side elevational view of an instrument in accordance with the present invention, showing opened jaws with deflated balloons.

FIG. 6 is a side elevational view similar to FIG. 5, showing opened jaws with inflated balloons.

FIG. 7 is a schematic perspective view showing a step in using the instrument assembly of FIGS. 1–4 to grasp a portion of a colon in a laparoscopic procedure.

FIG. 8 is a schematic perspective view showing a subsequent step in using the instrument assembly of FIGS. 1–4 to grasp a portion of a colon in a laparoscopic procedure.

DETAILED DESCRIPTION

Figure 1:
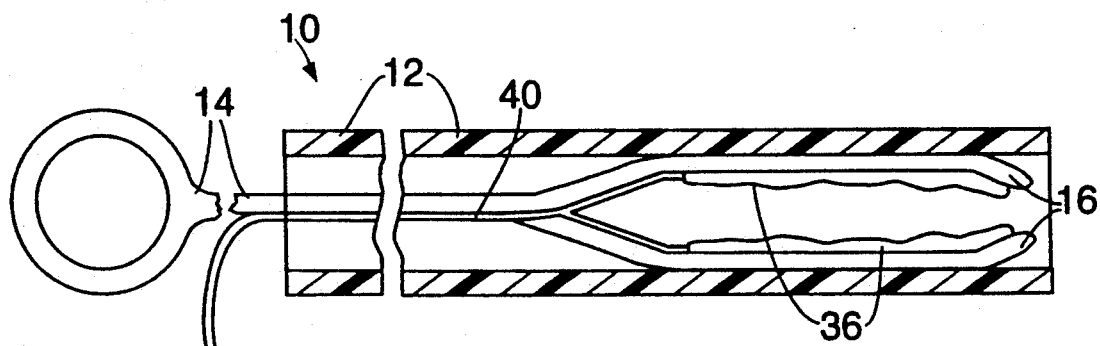
FIG. 1 is a partial longitudinal cross-sectional view of an instrument assembly in accordance with the present invention, showing a grasping or clamping member with a pair of prongs or jaws in a collapsed or closed configuration in the distal end of a tubular member, the jaws being provided with deflated balloons.
Figure 1:
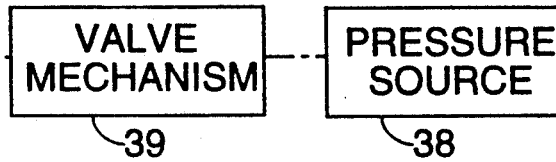

As illustrated in FIGS. 1–4, a surgical instrument assembly 10 particularly utilizable in laparoscopic procedures for grasping and temporarily displacing large internal organs such as a colonic section or a major blood vessel comprises an elongate essentially rigid tubular member 12 and an elongate substantially rigid rod 14 slidably inserted in the tubular member. Two prongs or arms 16 are connected to rod 14 at a distal end thereof for forming jaws of a substantially C-shaped clamping or grasping member 18 upon an ejection of the prongs from the distal end of tubular member 12 by a distally directed stroke of rod 14.

Prongs 16 are integral with rod 14 and with one another and are formed with an internal spring force tending to bias the prongs towards an opened or expanded configuration (FIGS. 2 and 3) in the absence of a closure force. Prongs 16 are made of a resilient material having a memory, i.e., a limited degree of flexibility, allowing a loading of the prongs into the distal end of tubular member 12 in a collapsed configuration (FIG. 1), subsequent expansion (FIG. 2), and partial closure during use of the instrument assembly to grasp and temporarily displace a colonic section or other large internal organ (FIG. 8).

The closure force for partially closing prongs or jaws 16 is supplied by tubular member 12. Tubular member 12 cooperates with prongs 16 in a camming action to press the prongs towards one another upon relative motion of the tubular member and the prongs towards each other.

Figure 2:
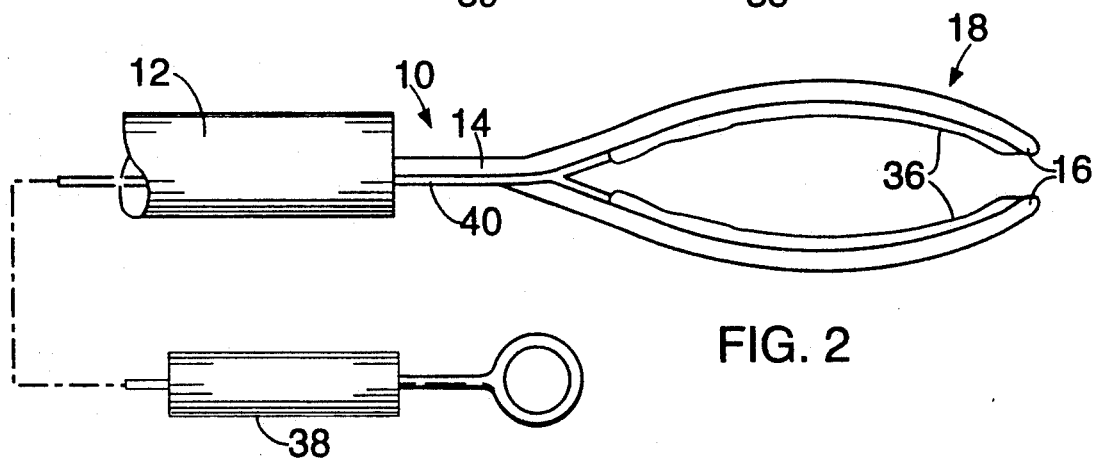
FIG. 2 is a schematic side elevational view of the instrument assembly of FIG. 1, showing the grasping or clamping member in an expanded or opened configuration and the balloons deflated, outside the distal end of the tubular member.
Figure 3:
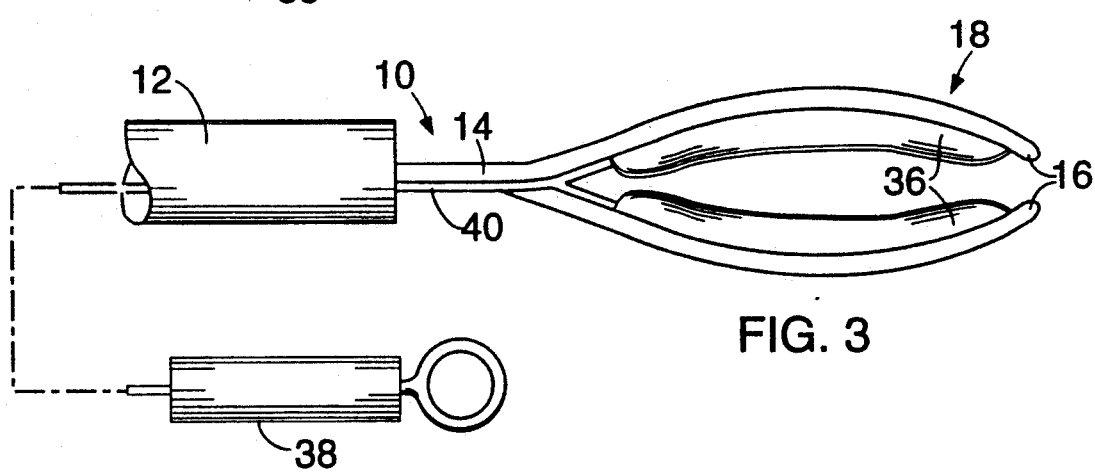
FIG. 3 is a schematic side elevational view similar to FIG. 2, showing the grasping or clamping member opened and the balloons inflated.

Prongs or jaws 16 are provided along concave inner sides with respective balloons 36. During an insertion of tubular member 12 into a patient via a laparoscopic trocar sleeve (see FIGS. 7 and 8), balloons 36 are in a deflated configuration, as illustrated in FIG. 1. After the ejection of prongs or jaws 16 from the distal end of tubular member 12 by an ejection stroke of rod 14, jaws 16 open automatically under the action of their internal spring biasing forces, as illustrated in FIG. 2. Balloons 36 are then inflated to a partially or fully expanded configuration, as illustrated in FIG. 3, by activating a pressure source 38 such as a hypodermic type syringe. Syringe 38 is initially filled with air or saline solution (FIG. 2) and communicates with balloons 36 via a duct or hollow line 40 extending along and connected to rod 14.

Figure 4:
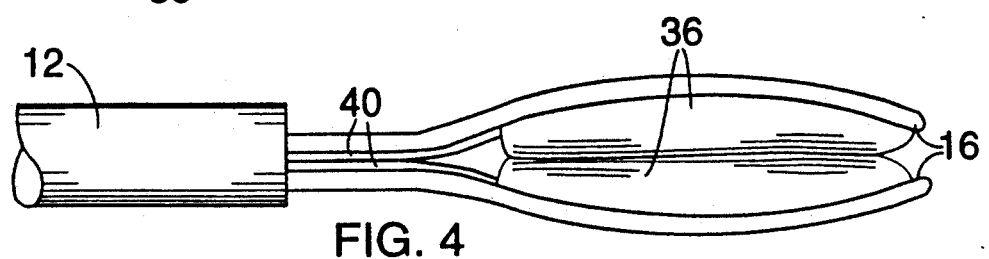
FIG. 4 is a view similar to FIGS. 2 and 3, showing the the grasping or clamping member partially closed and the balloons inflated.

A valve mechanism 39 may be provided in duct 40 for selectively blocking the flow of fluid along the duct, thereby locking balloons 26 in an inflated configuration, for example (FIGS. 3 and 4). Where pressure source 38 takes the form of a syringe (FIGS. 2 and 3), the valve mechanism may be effectuated by a detent (not shown) on the syringe.

Balloons 36 are inflated subsequently to a disposition of a patient's organ between jaws 16 during a surgical procedure. Accordingly, the insertion of the organ between jaws 16 is facilitated and the surgeon can better control the degree to which balloons 36 are inflated in order to match the size and pressure of the balloons to the organ section.

As illustrated in FIG. 4, upon inflation of balloons 36, tubular member 12 may be shifted in a distal direction relative to rod 14 to engage jaws 16 at their proximal ends in a camming action serving to press and partially close the jaws. Such a closure step is necessary in the event that the organ is relatively small.

In the modified embodiment of FIGS. 5 and 6, a modified surgical grasper assembly 20 includes an elongate essentially rigid tubular member 22 and an elongate substantially rigid rod 24 slidably inserted in the tubular member. A pair of prongs or arms 26 are connected to rod 24 at a distal end thereof for forming jaws of a substantially C-shaped clamping or grasping member 30 upon an ejection of the prongs from the distal end of tubular member 22 by a distally directed stroke of rod 24.

Prongs 26 are integral with rod 24 and with one another and are formed with an internal spring force tending to maintain the prongs in an opened or expanded configuration in the absence of a closure force. Prongs 26 consist of a resilient material having a memory which allows an alternate collapsing of the prongs into the forward end of tubular member 22 and an expanding of the prongs into an expanded configuration.

The closure force for partially closing prongs or jaws 26 is provided by tubular member 22. Tubular member 22 cooperates with prongs 26 in a camming action to press the prongs towards one another upon relative motion of the tubular member and the prongs towards each other.

Prongs or jaws 26 are provided along concave inner sides with respective balloons 42. During an insertion of tubular member 22 into a patient via a laparoscopic trocar sleeve (see FIGS. 7 and 8), balloons 42 are in a deflated configuration. After the ejection of prongs or jaws 26 from the distal end of tubular member 22 by an ejection stroke of rod 24, jaws 26 open automatically under the action of their internal spring biasing force. Balloons 42 are then inflated to a partially or fully expanded configuration, by activating a pressure source in the form of an auxiliary balloon 44 attached to rod 24 at a proximal end thereof. Balloon 44 is initially filled with air or saline solution (FIG. 5) and communicates with balloons 42 via a duct or hollow line 46 extending along and connected to rod 24.

Balloons 42 are inflated subsequently to a disposition of a patient's organ between jaws 26 during a surgical procedure. Accordingly, the insertion of the organ between jaws 26 is facilitated and the surgeon can better control the degree to which balloons 42 are inflated in order to match the size and pressure of the balloons to the organ section. Alternatively, in at least some cases, balloons 42 may be inflated prior to the disposition of the organ between jaws 26.

A clip 48 or other manually controllable valve element may be placed about duct 46 for enabling a blocking of communication along the duct, thereby locking balloons 42 in a desired state of inflation.

Prongs 16, 26 each have an arcuate configuration when ejected from a distal end of the respective tubular member 12, 22 by a distally directed motion of rod 14, 24. Prongs 16, 26 are flattened out and pressed towards one another when retracted into the distal end of tubular member 12, 22 by a proximally directed motion of rod 14, 24 or, alternatively, when tubular member 12, 22 is pushed in the distal direction over proximal end portions of the prongs.

Prongs 16, 24 have generally round edges to reduce, if not eliminate, the possibility of accidental cutting of internal organic tissues during use of the instrument assembly.

As depicted in FIG. 7, a distal end of tubular member 12 or 22 is inserted into a patient's abdominal cavity AC through a trocar sleeve 34 which has been positioned in the abdominal wall AW. During this insertion step, prongs 16 or 26, as well as collapsed balloons 36 or 42, are disposed in the distal end portion of the respective tubular member 12, 22. Upon insertion of tubular member 12 or 22 s that the distal end thereof protrudes into the abdominal cavity AC, rod 14 or 24 is pushed in the distal direction through tubular member 12, 22 to eject prongs 16 or 26 from the tubular member. Prongs 16 or 26 are spread apart under the action of their own internal spring forces to form a pair of generally C-shaped grasping and clamping jaws. The instrument assembly is then manipulated to move the jaws or prongs 16 or 26 towards an internal organ such as colonic section SC to insert a portion of the organ between the jaws. Prior to or after the manipulation of the instrument assembly to dispose the organ between jaws 16, 26, balloons 26, 42 are inflated to provide a cushioning function.

If necessary, tubular member 12, 22 is shifted towards prongs 16 or 26, as illustrated in FIG. 8, to cam against the prongs and thereby partially close the jaws or prongs 16, or 26 about the colonic section SC. Section SC may then be displaced relative to other organic tissues of the patient by exerting a force on jaws or prongs 16 or 26 via tubular member 12, 22 and rod 14, 24.

After the laparoscopic procedure utilizing the instrument assembly, tubular member 12, 22 is pulled in a proximal direction relative to rod 14, 24 to enable an opening of prongs 16, 26 under the action of their own internal spring forces. In addition, balloons 36, 42 are deflated. Upon a manipulation of the instrument assembly to remove the colonic section SC from the grasping and clamping jaws, prongs 16, 26 are then collapsed by pulling on rod 14, 24 relative to tubular member 12, 22 to draw the prongs back into the distal end of the tubular member.

Although the invention has been described in terms of particular embodiments and applications, one of ordinary skill in the art, in light of this teaching, can generate additional embodiments and modifications without departing from the spirit of or exceeding the scope of the claimed invention. It is to be noted, for example, that surgical instrument assemblies in accordance with the present invention may be utilized in operations other than laparoscopic surgery. Even in open abdominal surgery, it is frequently necessary to move an organ such as an intestine or an artery in order to reach an underlying organ.

It is to be additionally noted that in some cases, depending on the size of the organ to be grasped and the distance the organ is to be shifted, the inflation of the balloon elements 36, 42 on the jaws 16, 26 of the instrument may provide a sufficient clamping force so that the tubular member 12, 22 need not be used to press and flatten the arms or prongs.

Balloon elements 36 and 42 may take any of a number of equivalent forms. For example, a single balloon (not illustrated) with a generally C-shaped from may be attached to the prongs or jaws 16, 26. Additionally, or alternatively, the balloons may substantially surround the prongs or jaws 16, 26, rather than being disposed only along the concave inner surfaces thereof.

Furthermore, the jaws or prongs of grasping and clamping members of other surgical instruments may be provided with inflatable cushioning balloons in accordance with the present invention. For instance, the jaws may be linear, rather than arcuate, and spread by mechanisms other than an internal spring biasing force, such as a beveled screw device, a rack and pinion arrangement, a hydraulic circuit with a biasing spring, etc.

Accordingly, it is to be understood that the drawings and descriptions herein are profferred by way of example to facilitate comprehension of the invention and should not be construed to limit the scope thereof.

What is claimed is:

1. A surgical instrument assembly comprising:
   an elongate member provided at a distal end with a clamping member having a pair of opposed jaws;
   at least one balloon element attached to said jaws so as to form a cushion upon inflation of the balloon element;
   inflation means operatively connected to said balloon element for inflating same from a collapsed insertion configuration to an expanded use configuration; and
   closure means associated with and at least partially coextensive with said elongate member in a longitudinal direction for closing said clamping member about an object.

2. The instrument assembly defined in claim 1 wherein said arms are arcuate and said clamping member is generally C-shaped, said closure means operating to press said arms towards one another to partially flatten said arms, thereby closing said clamping member about an object.

3. The instrument assembly defined in claim 2 wherein said arms are integral with said elongate member and with one another, said arms being made of a resilient material having a limited degree of flexibility and an internal spring force whereby said arms are maintained in an opened configuration in the absence of a closure force.

4. The instrument assembly defined in claim 3 wherein said closure means includes a tubular member surrounding at least a portion of said elongate member, said tubular member cooperating with said arms in a camming action to press said arms towards one another upon relative motion of said tubular member and said arms towards each other.

5. The instrument assembly defined in claim 4 wherein said elongate member is a rod slidably inserted into said tubular member.

6. The instrument assembly defined in claim 1 wherein said balloon element is one of a pair of balloon elements each attached to a respective one of said jaws.

7. The instrument assembly defined in claim 1 wherein said inflation means includes an auxiliary balloon attached to said elongate member at a proximal end thereof.

8. A surgical instrument assembly comprising:
   an elongate tubular member;
   an elongate rod having at least a portion slidably inserted in said tubular member;
   two prongs connected to said rod at a distal end thereof, said prongs each having an arcuate configuration when ejected from a distal end of said tubular member by a distally directed motion of said rod, said prongs forming a pair of grasping jaws in the ejected configuration, said prongs being flattened out and pressed towards one another upon a shifting of the tubular member over the prongs at a proximal end thereof;
   at least one balloon element attached to said prongs so as to form a cushion upon inflation of the balloon element; and
   inflation means operatively connected to said balloon element for inflating same from a collapsed insertion configuration to an expanded use configuration.

9. A surgical method comprising the steps of:
   inserting a distal end of an elongate member into a patient's abdomen;
   upon said step of inserting, opening a pair of opposed arms of a clamping member connected to said elongate member at a distal end thereof, thereby forming a pair of jaws;
   moving said jaws towards an internal organ of the patient to insert a portion of said organ between said jaws; and
   inflating a balloon element connected to said jaws, thereby forming a cushion for clamping said organ.

10. The method defined in claim 9 wherein said arms are integral with said elongate member and with one another, said arms being made of a resilient material having a limited degree of flexibility and an internal spring force whereby said arms are maintained in an opened configuration in the absence of a closure force.

11. The method defined in claim 10, further comprising the step of pressing said jaws towards one another to partially flatten said jaws, thereby closing said clamping member about said organ.

12. The method defined in claim 11 wherein said step of pressing includes the step of shifting an elongate tubular member towards said jaws to engage said jaws in a camming action and to partially close said jaws in opposition to said internal spring force.

13. The method defined in claim 9 wherein said balloon element is in a collapsed configuration during said step of inserting.

14. The method defined in claim 9 wherein said balloon element is one of a pair of balloon elements attached to respective ones of said jaws, said step of inflating comprising the step of inflating said balloon elements simultaneously.

15. The method defined in claim 9 wherein said step of inflating is executed subsequently to said step of moving.

16. The method defined in claim 9 wherein said step of inflating is executed prior to said step of moving.

17. The method defined in claim 9 wherein said step of inserting includes the step of inserting said elongate member through a trocar sleeve into the patient's abdomen, said method being part of a laparoscopic procedure.

18. The method defined in claim 9, further comprising the step of displacing said organ relative to other organic tissues of the patient by exerting a force on said elongate member and said jaws upon completion of said step of inflating.

* * * * *